United States Patent [19]  [11]  4,342,702
Walker  [45]  Aug. 3, 1982

[54] METALLATED HALOGENATED ACETYLENE CORTICOID SYNTHESIS

[75] Inventor: Jerry A. Walker, Kalamazoo, Mich.

[73] Assignee: The Upjohn Company, Kalamazoo, Mich.

[21] Appl. No.: 264,759

[22] Filed: May 18, 1981

[51] Int. Cl.$^3$ .............................................. C07J 7/00
[52] U.S. Cl. ........................ 260/397.3; 260/397.45; 260/397.47; 260/397.4
[58] Field of Search ......................... 260/397.3, 397.45

[56] References Cited

U.S. PATENT DOCUMENTS 4,041,055  8/1977  Shephard et al. ................ 260/397.3
4,154,730  5/1979  Torelli et al. ................... 260/397.45
4,183,924  1/1980  Green et al. .................... 260/397.45

OTHER PUBLICATIONS

J. Am. Chem. Soc. 86, 3840 (1964).
D. E. O'Connor & W. I. Lyness, "The Effect of Methylmercapto, Methylsulfinyl, and Methylsulfonyl Groups on the Equilibrium in Three-Carbon Prototropic Systems".

Primary Examiner—Elbert L. Roberts
Attorney, Agent, or Firm—Bruce Stein

[57] ABSTRACT

A process for the preparation of corticoids (IX) which comprises reacting a 17-keto steroid (I) with a metallated halogenated acetylene (II) followed by reaction with a sulfenylating agent (IV) and $C_{17}$ side chain rearrangement.

20 Claims, No Drawings

METALLATED HALOGENATED ACETYLENE CORTICOID SYNTHESIS

DESCRIPTION

Background of the Invention

In the past few years, 17-keto steroids have become much more readily available as starting materials for corticoid synthesis because of the discovery of a mixture of microorganisms which will cleave the $C_{17}$ side chain of various steroid substrates, see U.S. Pat. Nos. 4,035,236, 3,684,657 and 3,759,791.

U.S. Pat. No. 4,041,055 claims a process for producing 17α-hydroxyprogesterone and corticoids from 17-keto steroids. The first step is addition of a 2-carbon moiety by formation of ethisterone. This is followed (1) by reaction with phenylsulfenyl chloride to form an allene sulfoxide, (2) Michael addition to form a sulfoxide, (3) reaction with a thiophile and (4) reaction with a peracid to give the 17α,21-dihydroxy-20-keto corticoid side-chain.

U.S. Pat. No. 4,216,159 claims a process of transforming a 17-keto steroid to the corresponding 16-unsaturated-21-hydroxy-20-keto steroid by reaction with a lithiated chlorovinyl ether. The objective of that patent is to produce $\Delta^{16}$-$C_{21}$ steroids which can then be used to make $C_{16}$ functionalized corticoids.

The process of the present invention does not involve lithiated chloro vinyl ethers and does not produce $\Delta^{16}$-$C_{21}$ steroids.

The process of the present invention is similar to the process of U.S. Pat. No. 4,041,055 in that it transforms a 17-keto steroid to the corresponding corticoid, but does so by a different synthetic pathway.

The base catalyzed isomerization of $\beta,\gamma$ to $\alpha,\beta$-unsaturated sulfoxides is well known, see J. Am. Chem. Soc. 86, 3840 (1964).

SUMMARY OF THE INVENTION

Refer to Charts A–C.

Disclosed is a process for the preparation of a 21-halo allene sulfoxide of formula (V) which comprises contacting a 17α-haloethynyl steroid of formula (III) with a sulfenylating agent of the formula $R_{22}$-S-X (IV).

Also disclosed is a process for the preparation of a sulfoxide of formula (VI) which comprises (1) contacting a 21-halo allene sulfoxide of formula (V) with a base selected from the group consisting of $OR_{20}$ and $SR_{20}$ and (2) quenching with an acid.

Further disclosed is the 21-halo allene sulfoxide (V).

DETAILED DESCRIPTION OF THE INVENTION

The 17-keto steroid starting materials are well known to those skilled in the art or may readily be prepared from known compounds by methods well known to those skilled in the art. For example, the $\Delta^{1,4}$-17-keto steroids are known, see U.S. Pat. No. 2,902,410, in particular Example 1. The $\Delta^{4,9(11)}$-17-keto steroids are known, see U.S. Pat. No. 3,441,559, in particular Example 1. The 6α-fluoro-17-keto steroids are known, see U.S. Pat. No. 2,838,492, in particular Examples 9 and 10. The 6α-methyl-17-keto steroids are known, see U.S. Pat. No. 3,166,551, in particular Example 8. See also U.S. Pat. Nos. 2,867,630 and 3,065,146.

The 16β-methyl-17-keto steroids can readily be prepared from the corresponding 17-keto steroid by the processes of U.S. Pat. No. 3,391,169 (Examples 75, 76), U.S. Pat. No. 3,704,253 (column 2 and Examples 1–3) and U.S. Pat. No. 3,275,666.

Charts A and B disclose the process of the present invention.

Chart A discloses the addition of the metallated halogenated acetylene:

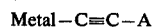

$$\text{Metal}-C \equiv C-A \qquad (II)$$

to a protected 17-keto steroid (Ia–Ie) to give the corresponding 17α-haloethynyl steroid (III), respectively, and its subsequent transformation to the 21-halo allene sulfoxide (V).

The 17-keto steroid is usually protected at the C-3 position before reaction with the metallated halogenated acetylene (II). However, it is known to those skilled in the art that in some cases the reaction can be carried out without protection. See Organic Reactions in Steroid Chemistry, Fried, Vol. II, p. 136. The use of protected derivatives is more generally applicable for a wide range of 17-keto steroids. The androst-4-ene-3,17-diones are protected as the 3-enol ether (Ia), 3-enamine (Ib) or ketal (Ic), see Chart C, where $R_3$ is alkyl of 1 thru 5 carbon atoms, with the proviso that with the ketal the $R_3$ groups can be connected to form the ethylene ketal; $R_3'$ and $R_3''$ are the same or different and are alkyl of 1 thru 5 carbon atoms. The enol ethers (Ia) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The 3-enamines (Ib) are also prepared by methods well known in the art, see U.S. Pat. No. 3,629,298 and Steroid Reactions, supra, page 49–53. The ketals (Ic) are also prepared by well known methods, see Steroid Reactions, supra, page 11–14. The androsta-1,4-diene-3,17-diones are protected as the 3-dialkylenamine (Id) or ketal (Ie), see Chart C.

In Chart A, the compound of formula (Ia) can be replaced by either the compound of formula (Ib or Ic), all of which by the process of the present invention will produce the corresponding intermediate compound of the formula (III), respectively, and the same 21-halo allene sulfoxide (V). Likewise with the $\Delta^1$ steroids, the compound of formula (Id) can be replaced by the compound of formula (Ie), which by the process of the present invention will produce the corresponding intermediate compound of the formula (III).

Metallated halogenated acetylenes of the formula:

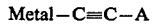

$$\text{Metal}-C \equiv C-A \qquad (II)$$

where metal is sodium, potassium or lithium and A is a fluorine, chlorine or bromine atom are known. See Organic Reactions in Steroid Chemistry, Fried, Vol. II, p. 136. It is preferred that metal be lithium and A be a bromine or chlorine atom. It is more preferred that A is a chlorine atom, lithium chloroacetylene is known, see Fried, p. 138.

The ethynylation of protected 17-keto steroids (Ia–Ie) utilizing metallated halogenated acetylenes (II) to produce 17α-haloethynyl steroids (III) is known, see Fried, supra.

Chart A discloses the sulfenylation of the 17α-haloethynyl steroid (III) to produce the sulfoxide (V) by use of the sulfenylating agent $R_{22}$-S-X (IV) where $R_{22}$ is alkyl of 1 thru 5 carbon atoms, trichloromethyl, phenyl, or phenyl substituted with 1 thru 4 carbon atoms or substituted with 1 thru 3 nitro or trifluoromethyl groups, aralkyl of 7 thru 12 carbon atoms, or —N—$(R_{122})_2$ where $R_{122}$ is alkyl of 1 thru 4 carbon atoms or phenyl, or phthalimide. It is preferred that $R_{22}$ is phenyl. The group X is a chlorine or bromine atom or phenylsulfone, phthalimide or imidazole group, it is preferred that X is chlorine or bromine atom, and it is more preferred that X is chlorine.

The appropriately substituted sulfenylating agents (IV) are prepared by methods known to those skilled in the art. For example, sulfuryl chloride is added to a thiol previously dissolved in an organic solvent such as carbon tetrachloride. See Chem. Reviews, 39, 269 (1946) at page 279 and U.S. Pat. No. 2,929,820.

The sulfenylation reaction is carried out in a non-polar aprotic solvent such as toluene, chloroform, ether, or methylene chloride. The reaction is carried out in the presence of at least an equal molar amount of a tertiary amine base, such as triethylamine or pyridine. With triethylamine, preferably an excess is used. Any excess base serves as additional solvent for the reaction. The reaction is preferably carried out at about $-15°$ to $0°$, but proceeds adequately in a temperature range of about $-80°$ to about $25°$. The reaction is preferably carried out under an inert dry gas such as nitrogen, argon, or carbon dioxide. The substituted sulfenyl halide (IV) is added dropwise to the reaction mixture. Following addition of the substituted sulfenylating agent to the reaction mixture, the cooling bath is removed and the temperature is allowed to rise to about $20°$; however, the temperature may be in the range of about $-30°$ to about $25°$. The excess substituted sulfenylating agent is then quenched with an appropriate quenching agent such as water, cyclohexene, various alcohols such as methanol and ethanol, or acetone. The reaction is then washed with dilute acid such as 1 N hydrochloric, sulfuric, phosphoric, acetic, etc. The concentration of the acid is not critical. The excess acid is removed with agents which are well known in the art such as sodium bicarbonate. The solvent is then removed and the product may be obtained by standard work-up.

The 21-halo allene sulfoxide (V) is transformed to the corresponding sulfoxide (VI) by reaction with base. At least one equivalent of a base or anion such as $\ominus OR_{20}$ or $\ominus SR_{20}$ is used where $R_{20}$ is alkyl of 1 thru 4 carbon atoms or phenyl. The preferred bases are methoxide, ethoxide, or phenoxide. Methoxide is most preferred. The reaction requires a polar solvent such as DMSO, DMF, THF to proceed at a good rate. The reaction goes in alcoholic solvents but proceeds more slowly.

The sulfoxide (VI) can be isolated from the above reaction by quenching and normal work-up; however, it is preferable not to isolate the sulfoxide (VI) but rather perform the next reaction, conversion of sulfoxide (VI) to the corresponding 20-unsaturated steroid (VII), in situ. If one desires to isolate the sulfoxide (VI), one equivalent base is used and the preferred solvents are DMF or THF. After addition is complete, as measured by TLC, the reaction is quenched by addition of a mild acid and is worked up as is well known to those skilled in the art.

If the preferred route is followed without isolation of the sulfoxide (VI), 1.5–2.0 equivalents of base are used. In addition, the preferred solvent system is THF-acetone-methanol. Acetone acting as both a solvent and thiophile. The 21-halo allene sulfoxide (V) is cooled to about $0°$, the base is added, and the sulfoxide (VI) forms rapidly in about 5 minutes. The mixture is warmed to $20°$–$40°$, more preferably $25°$–$30°$ and is stirred 6–20 hours and then quenched with acid.

The sulfoxide (VI) exists as four isomers, only one of which gives exclusively the desired 20-unsaturated steroid (VII), the rest give a mixture of the desired 20-unsaturated steroid (VII) and the undesired 17$\beta$-hydroxy steroids. Apparently these four isomers are in equilibrium with each other and the most reactive isomer yields the desired 20-unsaturated steroid (VII). The base catalyzed isomerization of $\beta$, $\gamma$ to $\alpha,\beta$-unsaturated sulfoxides is well known, see J. Am. Chem. Soc. 86, 3840 (1964). Therefore, it is desired to use a polar solvent system in the presence of base to continuously equilibrate the undesired three isomers to produce the desired isomer as it is converted to the 20-unsaturated steroid (VII).

During the reaction involving the conversion of the sulfoxide (VI) to the corresponding 20-unsaturated steroid (VII) it is necessary to trap the $R_{22}$-$S^{\oplus}$ moiety. Therefore, the reaction necessitates the use of thiophiles. The thiophile must not be nucleophilic or the Z group will be lost. Suitable thiophiles include ketones (acetone, 3-pentanone, cyclohexanone, 1-(phenylthio)acetone, 2,4-pentanedione), phosphites (trimethylphosphite), mesityl oxide, dimethyl malonate, 2,6-di-t-butylphenol, ethyl vinyl ether and dihydropyran. Ketones are preferred and acetone is the preferred ketone.

The 20-unsaturated steroid (VII) is transformed to the corresponding 21-halo steroid (VIII) by aqueous acid (p-TSA, hydrochloric, sulfuric or phosphoric) hydrolysis. Aqueous hydrochloric acid in methylene chloride is preferred.

The 21-halo steroid (VIII) is transformed to the corresponding corticoid (IX) by the process of U.S. Pat. No. 4,041,055, see column 15, lines 39–56. If the substituent at $C_{21}$ is chlorine rather than bromine, potassium iodide can be used as a catalyst. The preferred anion is acetate.

The 21-acyloxy-17$\alpha$-hydroxy-20-keto end products (IX) are useful pharmacologically active steroids and are useful intermediates in the production of other pharmacologically active corticoids. For example, 17$\alpha$,21-dihydroxypregna-4,9(11)-diene-3,20-dione 21-acetate (IX), the compound produced by Example 6, is an important intermediate in corticoid synthesis as evidenced by the fact that U.S. Pat. No. 3,444,559 (Examples 2, 8 and 9) and U.S. Pat. No. 4,041,055 (Example 66 and claims 91 and 92) disclose and claim its production.

DEFINITIONS

The definitions and explanations below are for the terms as used throughout the entire patent application including both the specification and claims.

All temperatures are in degrees Centigrade.
TLC refers to thin-layer chromatography.
THF refers to tetrahydrofuran.
DMSO refers to dimethylsulfoxide.
DMF refers to dimethylformamide.
p-TSA refers to p-toluenesulfonic acid.
NMR refers to nuclear (proton) magnetic resonance spectroscopy, chemical shifts are reported in ppm ($\delta$) downfield from TMS.
TMS refers to tetramethylsilane.
When solvent pairs are used, the ratio of solvents used are volume/volume (v/v).
A is a fluorine, chlorine or bromine atom.
R is alkyl of 1 thru 5 carbon atoms or phenyl.

R$_3$ is alkyl of 1 thru 5 carbon atoms with the proviso that with the ketal (IIIc and IIIe), the R$_3$ groups can be connected to form the ethylene ketal.

Metal is lithium, sodium or potassium.

R$_3'$ is alkyl of 1 thru 5 carbon atoms.

R$_3''$ is alkyl of 1 thru 5 carbon atoms.

R$_6$ is a hydrogen or fluorine atom or methyl group.

R$_9$ is a hydrogen, or fluorine atom, hydroxyl group, —OSi(R)$_3$ or nothing.

R$_{11}$ is [H], [H,H], [H, β—OH], [H, βO—Si(R)$_3$] or [O].

R$_{16}$ is a hydrogen atom or methyl group.

R$_{20}$ is alkyl of 1 thru 4 carbon atoms or phenyl.

R$_{21}$ is alkyl of 1 thru 4 carbon atoms or phenyl.

R$_{22}$ is alkyl of 1 thru 5 carbon atoms, trichloromethyl, phenyl, phenyl substituted with 1-4 carbon atoms or substituted with 1 thru 3 nitro or trifluoromethyl groups, aralkyl of 7 thru 12 carbon atoms or —N—(R$_{122}$)$_2$ or phthalimide.

R$_{122}$ is alkyl of 1 thru 4 carbon atoms, phenyl, or phthalimide.

X is a chlorine or bromine atom, phenylsulfone, phthalimide or imidazole group.

Z is —OR$_{20}$ or —SR$_{20}$.

~ indicates the attached group can be in either the α or β configuration.

== is a single or double bond.

When the term "alkyl of ___ thru ___ carbon atoms" is used, it includes isomers thereof when such exist.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

17α-(chloroethynyl)-17β-hydroxyandrosta-4,9(11)-dien-3-one (III)

1,2-Dichloroethylene (18 ml) and dry THF (100 ml) are cooled to −30° under nitrogen. n-Butyllithium (1.6 M, 76 ml) is added drop-wise over 50 min. The mixture (II) is brought to −20° and stirred for 4 hr. 3β-Hydroxyandrosta-3,5,9(11)-trien-3-one 3-methyl ether (Ia, U.S. Pat. No. 3,516,991, 10 g) is added all at once. The mixture is stirred at −20° to −30° for 1.5 hr. and then quenched by the dropwise addition of aqueous hydrochloric acid (6 N, 10.5 ml). The mixture is brought to 20°–25° and stirred for 15 hr. Water (200 ml) is added and the mixture extracted with ethyl acetate (2×100 ml). The organic extracts are combined and backwashed with water (50 ml), dried over sodium sulfate and concentrated under reduced pressure to give the title compound, NMR (CDCl$_3$) 0.87, 1.37, 5.60 and 5.77δ.

EXAMPLE 2

21-Chloro-21-(phenylsulfinyl)pregna-4,9(11),17(20),20-tetraen-3-one (V)

17α-(Chloroethynyl)-17β-hydroxyandrosta-4,9(11)-dien-3-one (III, Example 1, 500 mg) and triethylamine (0.81 ml) are cooled to −15° to −20° under nitrogen and a solution of phenylsulfenyl chloride (IV, 250 mg) in methylene chloride (0.7 ml) is added dropwise. After stirring for 1 hr the mixture is brought to about 0° and acetone (0.5 ml) is added. The resulting mixture is diluted with water (20 ml) and extracted with methylene chloride (2×15 ml). The organic extracts are combined and backwashed with water (20 ml), dried over sodium sulfate and concentrated under reduced pressure to give the title compound, m.p. 210°–213°; NMR (CDCl$_3$) 1.02, 1.04, 1.38, 5.55, 5.77 and 7.3–7.8δ.

EXAMPLE 3

21-Chloro-20-methoxy-21-(phenylsulfinyl)pregna-4,9(11),17(20)-trien-3-one (VI)

21-Chloro-21-(phenylsulfinyl)pregna-4,9(11),17(20),20-tetraen-3-one, (V, Example 2, 100 mg) and THF (1 ml) are slurried and cooled to 0°–5° under nitrogen. Sodium methoxide in methanol (25%, 0.05 ml) is added with stirring. The mixture is stirred 1 hr and then quenched with water (10 ml). The mixture is extracted with ethyl acetate (2×15 ml). The organic extracts are combined, backwashed with water (10 ml), dried over sodium sulfate and concentrated under reduced pressure to give the title compound.

EXAMPLE 4

21-Chloro-17α-hydroxy-20-methoxypregna-4,9(11),20-trien-3-one (VII)

To a solution of 21-chloro-20-methoxy-21-(phenylsulfinyl)pregna-4,9(11),17(20)-trien-3-one (VI, Example 3, 100 mg) in THF (2 ml), methanol (0.45 ml) and acetone (0.3 ml) at 0° under nitrogen is added a solution of sodium hydroxide (5 N, 0.04 ml). The mixture is brought to 20°–25° and is allowed to stir for 24 hr. The mixture is poured into a mixture of water (25 ml) and methylene chloride (10 ml). The layers are separated and the aqueous layer is extracted with methylene chloride (2×5 ml). The organic extracts are combined and washed with water (10 ml), dried over sodium sulfate and concentrated under reduced pressure to give the title compound.

EXAMPLE 5

21-Chloro-17α-hydroxypregna-4,9(11)-diene-3,20-dione (VIII)

21-Chloro-17α-hydroxy-20-methoxypregna-4,9(11),20-trien-3-one (VII, Example 4, 1.0 g), THF (4 ml), acetone (4.9 ml), and methanol (1.4 ml) are mixed. Aqueous hydrochloric acid (6 N, 0.44 ml) is added and the resulting slurry heated at 40° for 1.5 hours. The mixture is cooled to 20°–25° and diluted with hexane (3 ml). The solids are isolated by filtration and washed with hexane/ethyl acetate (85/15, 13 ml) to give the title compound.

EXAMPLE 6

17α,21-Dihydroxypregna-4,9(11)-diene-3,20-dione 21-acetate (IX)

21-Chloro-17α-hydroxypregna-4,9(11)-diene-3,20-dione (VIII, Example 5, 1.0 g), anhydrous potassium acetate (340 mg), potassium iodide (114 mg), anhydrous acetone (7.5 ml) and methylene chloride (2.5 ml) are slurried and heated to 70° (closed to the atmosphere—therefore under slight pressure) for 5 to 7 hours. The reaction mixture is cooled to 20°–25° and the methylene chloride removed under reduced pressure. Acetone (3.5 ml) is added, followed by water (1.5 ml). The mixture is heated to about 70° for 30 minutes, then cooled to 0° for about 2 hours. The product is isolated by filtration and then washed with water (5 ml) and aqueous acetone (80%, 5 ml). After drying, the title compound is obtained, NMR (CDCl₃) 0.64, 1.33, 2.18, 4.97, 5.56 and 5.75δ.
CHART A
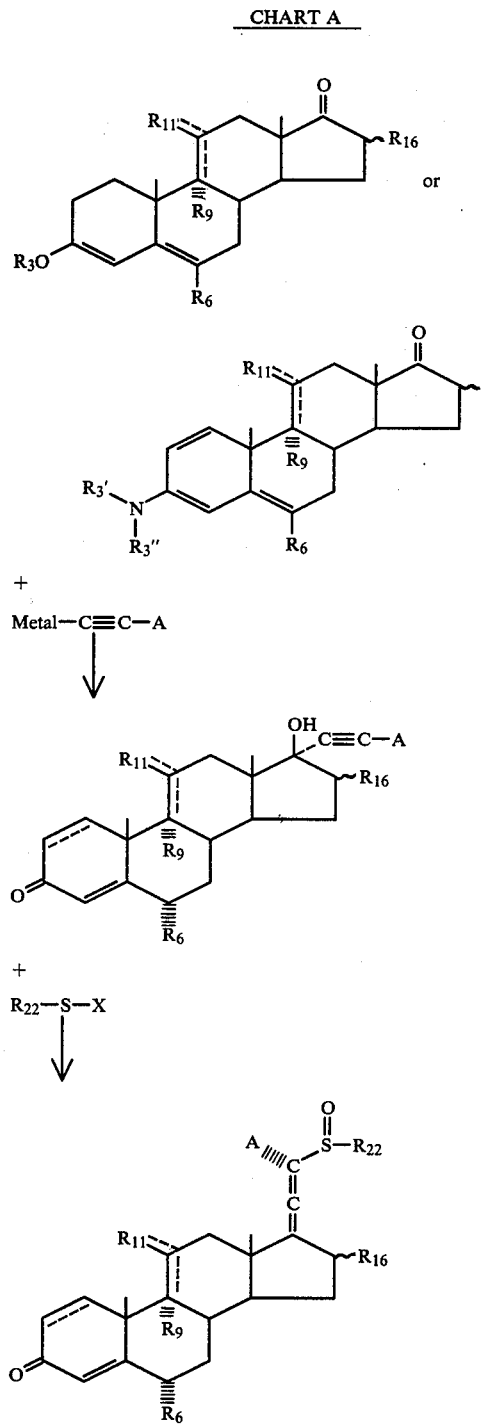
CHART B
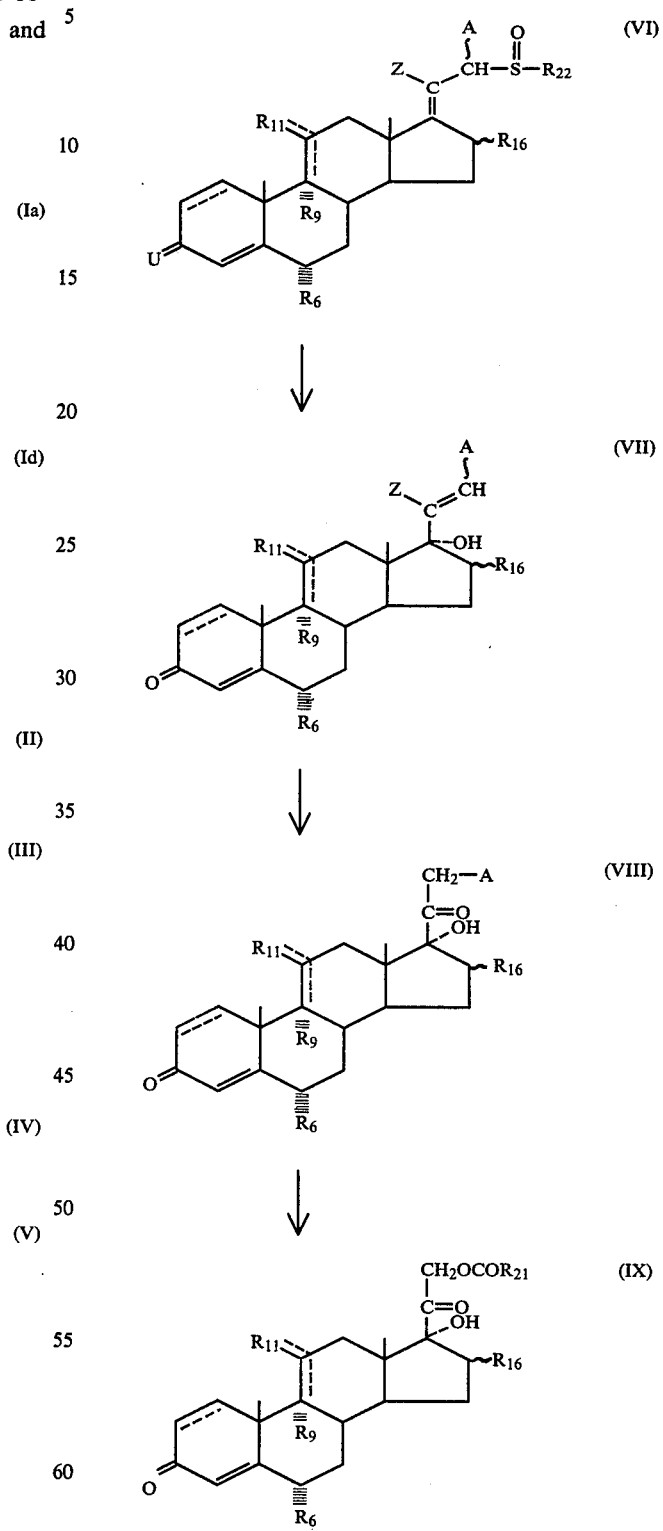
CHART C -continued

CHART C

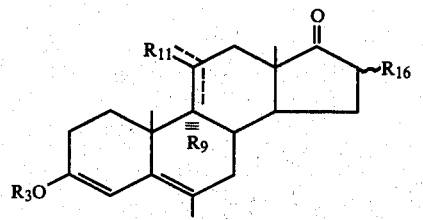
(Ia)

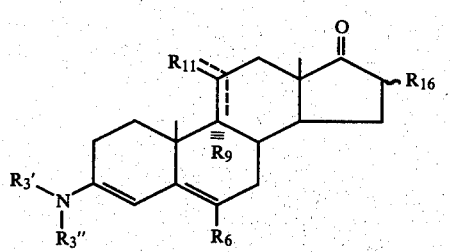
(Ib)

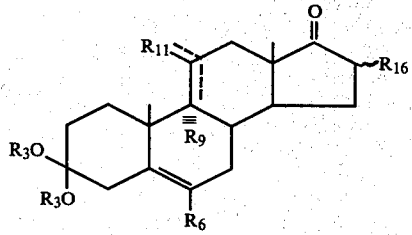
(Ic)

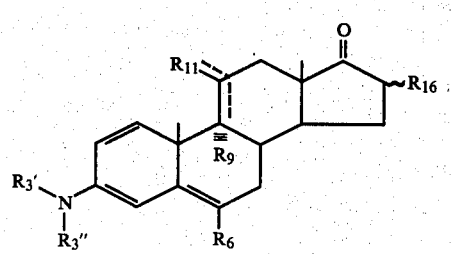
(Id)

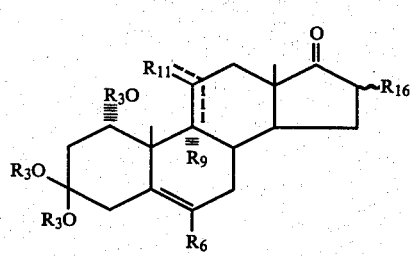
(Ie)

I claim:

1. A 21-halo allene sulfoxide of the formula:

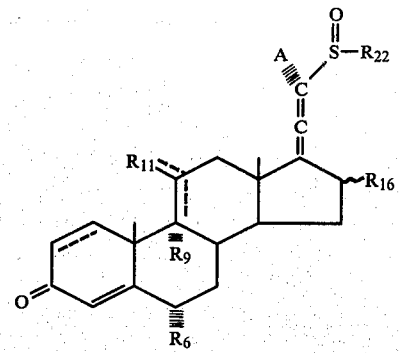
(V)

where A, $R_6$, $R_9$, $R_{11}$, $R_{16}$, $R_{22}$, ~ and are defined in the specification.

2. A 21-halo allene sulfoxide according to claim 1 where $R_6$ is a hydrogen atom.

3. A 21-halo allene sulfoxide according to claim 1 where $R_{16}$ is a hydrogen atom.

4. A 21-halo allene sulfoxide according to claim 1 where $R_9$ is nothing and $R_{11}$ is [H] which gives a $\Delta^{9(11)}$ functionality in the C ring.

5. A 21-halo allene sulfoxide according to claim 1 where A is a chlorine atom.

6. A 21-halo allene sulfoxide according to claim 1 where $R_{22}$ is phenyl.

7. A 21-halo allene sulfoxide according to claim 1 which is 21-chloro-21-(phenylsulfinyl)pregna-4,9(11),17(20),20-tetraen-3-one.

8. A process for the preparation of a 21-halo allene sulfoxide of the formula:

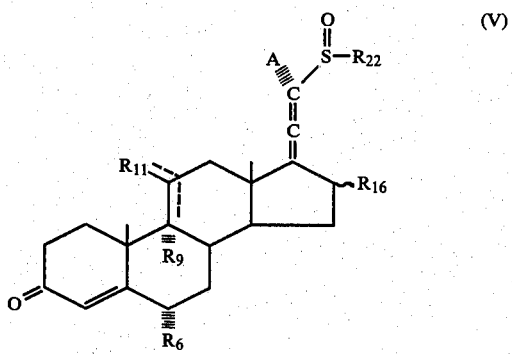
(V)

which comprises contacting a 17α-haloethynyl steroid of the formula:

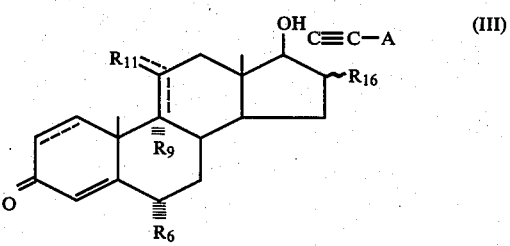
(III)

with a sulfenylating agent of the formula:

$R_{22}$—S—X (IV)

where A, $R_6$, $R_9$, $R_{11}$, $R_{16}$, $R_{22}$, X, ~ and are defined in the specification.

9. A process according to claim 8 where $R_{22}$ is phenyl and X is a chlorine or bromine atom.

10. A process according to claim 8 where $R_6$ is a hydrogen atom.

11. A process according to claim 8 where $R_{16}$ is a hydrogen atom.

12. A process according to claim 8 where $R_9$ is nothing and $R_{11}$ is [H] which gives a $\Delta^{9(11)}$ functionality in the C ring.

13. A process according to claim 8 where the 21-halo allene sulfoxide (V) is 21-chloro-21-(phenylsulfinyl)-pregna-4,9(11),17(20),20-tetraen-3-one.

14. A process for the preparation of a sulfoxide of the formula:

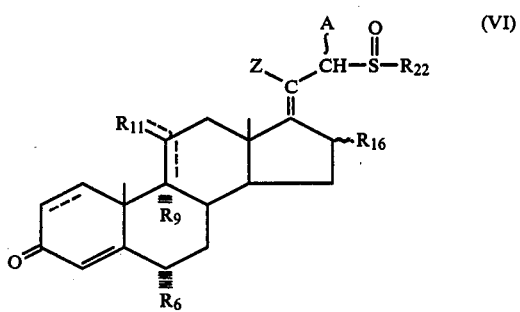

which comprises (1) contacting a 21-halo allene sulfoxide of the formula:

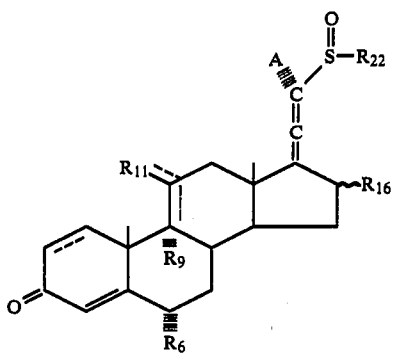

with a base selected from the group consisting of $OR_{20}$ and $SR_{20}$ and (2) quenching with an acid where A, $R_6$, $R_9$, $R_{11}$, $R_{16}$, $R_{20}$, $R_{22}$, Z, ~ and
are defined in the specification.

15. A process according to claim 14 where the base is methoxide, ethoxide or phenoxide.

16. A process according to claim 14 where 1.0 equivalents of base are used.

17. A process according to claim 14 where the acid is selected from the group consisting of p-TSA, hydrochloric acid, sulfuric acid, phosphoric acid, acetic acid or formic acid.

18. A process according to claim 14 where $R_6$ is a hydrogen atom.

19. A process according to claim 14 where $R_{16}$ is a hydrogen atom.

20. A process according to claim 14 where $R_9$ is nothing and $R_{11}$ is [H], which gives a $\Delta^{9(11)}$ functionality in the C ring.

* * * * *

UNITED STATES PATENT OFFICE
CERTIFICATE OF CORRECTION

Patent No. 4,342,702          Dated August 3, 1982

Inventor(s) Jerry A. Walker

It is certified that error appears in the above-identified patent and that said Letters Patent are hereby corrected as shown below:

Col. 10, line 17: "and   are defined" should read: -- and .... are defined --.
Col. 10, line 55, Formula III should appear as follows instead of as in the patent:

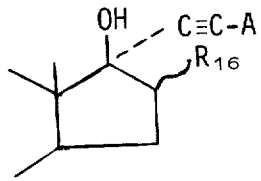

Col. 10, line 68, Col. 11, line 1: "and   are defined" should read: -- and .... are defined --.
Col. 12, line 21: "and   are defined" should read: -- and .... are defined --.

Signed and Sealed this

Sixteenth Day of August 1983

[SEAL]

Attest:

Attesting Officer

GERALD J. MOSSINGHOFF

Commissioner of Patents and Trademarks